US008831260B2

(12) United States Patent
Parker

(10) Patent No.: US 8,831,260 B2
(45) Date of Patent: Sep. 9, 2014

(54) BONE CONDUCTION HEARING DEVICE HAVING ACOUSTIC FEEDBACK REDUCTION SYSTEM

(75) Inventor: John L. Parker, Roseville (AU)

(73) Assignee: Cochlear Limited, Macquarie University (AU)

( * ) Notice: Subject to any disclaimer, the term of this patent is extended or adjusted under 35 U.S.C. 154(b) by 956 days.

(21) Appl. No.: 12/251,443

(22) Filed: Oct. 14, 2008

(65) Prior Publication Data

US 2009/0247814 A1 Oct. 1, 2009

Related U.S. Application Data

(60) Provisional application No. 61/041,185, filed on Mar. 31, 2008.

(51) Int. Cl.
*H04R 25/00* (2006.01)
*A61M 5/142* (2006.01)

(52) U.S. Cl.
CPC .......... *H04R 25/606* (2013.01); *H04R 2460/13* (2013.01); *H04R 25/70* (2013.01); *A61M 2210/0662* (2013.01); *A61M 5/14276* (2013.01); *A61M 2205/05* (2013.01)
USPC ........................................ 381/326

(58) Field of Classification Search
USPC ........................................... 381/326; 361/326
See application file for complete search history.

(56) References Cited

U.S. PATENT DOCUMENTS

| | | | | |
|---|---|---|---|---|
| 4,612,915 A * | 9/1986 | Hough et al. | ................... | 600/25 |
| 4,628,907 A * | 12/1986 | Epley | ............... | 600/25 |
| 6,137,889 A * | 10/2000 | Shennib et al. | ............... | 381/328 |
| 6,381,336 B1 * | 4/2002 | Lesinski et al. | ............... | 381/326 |
| 6,631,197 B1 * | 10/2003 | Taenzer | ........................ | 381/316 |
| 6,681,022 B1 * | 1/2004 | Puthuff et al. | ................ | 381/338 |
| 6,879,693 B2 * | 4/2005 | Miller et al. | .................... | 381/60 |
| 6,940,989 B1 * | 9/2005 | Shennib et al. | ............... | 381/326 |
| 7,043,040 B2 * | 5/2006 | Westerkull | .................... | 381/326 |
| 7,214,179 B2 * | 5/2007 | Miller et al. | .................... | 600/25 |
| 7,486,798 B2 * | 2/2009 | Anjanappa et al. | ........... | 381/151 |
| 7,564,988 B2 * | 7/2009 | Azima et al. | .................. | 381/326 |
| 7,616,771 B2 * | 11/2009 | Lenhardt et al. | ............. | 381/326 |
| 2005/0249366 A1 * | 11/2005 | Westerkull | .................... | 381/151 |

* cited by examiner

*Primary Examiner* — Eugene Lee
(74) *Attorney, Agent, or Firm* — K&L Gates LLP

(57) ABSTRACT

A bone anchored hearing device, comprises: a housing, a sound input element positioned in the housing configured to receive sound signals, and a transducer positioned in the housing configured to generate vibrations representative of the sound signals received by the sound input device.

15 Claims, 12 Drawing Sheets

BONE CONDUCTION HEARING DEVICE HAVING ACOUSTIC FEEDBACK REDUCTION SYSTEM

CROSS-REFERENCE TO RELATED APPLICATIONS

This application claims the benefit of U.S. Provisional Application No. 61/041,185, entitled "Bone Conduction Devices For The Rehabilitation OF Hearing Disorders," filed Mar. 31, 2008. This application is hereby incorporated by reference herein.

BACKGROUND

1. Field of the Invention

The present invention relates generally to bone anchored hearing devices, and more particularly, to bone anchored hearing devices having a feedback reduction system.

2. Related Art

Hearing loss, which may be due to many different causes, is generally of two types, conductive or sensorineural. In many people who are profoundly deaf, the reason for their deafness is sensorineural hearing loss. This type of hearing loss is due to the absence or destruction of the hair cells in the cochlea which transduce acoustic signals into nerve impulses. Various prosthetic hearing implants have been developed to provide individuals who suffer from sensorineural hearing loss with the ability to perceive sound. One such prosthetic hearing implant is referred to as a cochlear implant. Cochlear implants use an electrode array implanted in the cochlea of a recipient to bypass the mechanisms of the ear. More specifically, an electrical stimulus is provided via the electrode array directly to the cochlea nerve, thereby causing a hearing sensation.

Conductive hearing loss occurs when the normal mechanical pathways to provide sound to hair cells in the cochlea are impeded, for example, by damage to the ossicular chain to ear canal. However, individuals who suffer from conductive hearing loss may still have some form of residual hearing because the hair cells in the cochlea are may remain undamaged.

Individuals who suffer from conductive hearing loss are typically not candidates for a cochlear implant due to the irreversible nature of the cochlear implant. Specifically, insertion of the electrode array into a recipient's cochlea exposes the recipient to risk of the destruction of the majority of hair cells within the cochlea. The destruction of the cochlea hair cells results in the loss of all residual hearing by the recipient.

Rather, individuals suffering from conductive hearing loss typically receive an acoustic hearing aid, referred to as a hearing aid herein. Hearing aids rely on principles of air conduction to transmit acoustic signals through the outer and middle ears to the cochlea. In particular, a hearing aid typically uses an arrangement positioned in the recipient's ear canal to amplify a sound received by the outer ear of the recipient. This amplified sound reaches the cochlea and causes motion of the cochlea fluid and stimulation of the cochlea hair cells.

Unfortunately, not all individuals who suffer from conductive hearing loss are able to derive suitable benefit from hearing aids. For example, some individuals are prone to chronic inflammation or infection of the ear canal and cannot wear hearing aids. Other individuals have malformed or absent outer ear and/or ear canals as a result of a birth defect, or as a result of medical conditions such as Treacher Collins syndrome or Microtia. Furthermore, hearing aids are typically unsuitable for individuals who suffer from single-sided deafness (total hearing loss only in one ear). Cross aids have been developed for single sided deaf individuals. These devices receive the sound from the deaf side with one hearing aid and present this signal (either via a direct electrical connection or wirelessly) to a hearing aid which is worn on the opposite side. The disadvantage of this technology is the need for the individual to wear two hearing aids and suffer the complications of hearing aid use.

When an individual having fully functional hearing receives an input sound, the sound is transmitted to the cochlea via two primary mechanisms: air conduction and bone conduction. As noted above, hearing aids rely primarily on the principles of air conduction. In contrast, other devices, referred to as bone conduction devices, rely predominantly on vibration of the bones of the recipients skull to provide acoustic signals to the cochlea.

Those individuals who cannot derive suitable benefit from hearing aids may benefit from bone conduction devices. Bone conduction devices function by converting a received sound into a mechanical vibration representative of the received sound. This vibration is then transferred to the bone structure of the skull, causing vibration of the recipient's skull. This skull vibration results in motion of the fluid of the cochlea. Hair cells inside the cochlea are responsive to this motion of the cochlea fluid, thereby generating nerve impulses resulting in the perception of the received sound.

A known alternative to a normal air conduction hearing aid is a bone conduction hearing aid which uses a hearing aid to drive a vibrator which is pushed against the skull via a mechanism, such as glasses or wire hoops. These devices are generally uncomfortable to wear and, for some recipients, are incapable of generating sufficient vibration to accurately present certain received sounds to a recipient.

In one aspect of the present invention, a bone conduction hearing device is disclosed, the device comprising: a first housing comprising a sound input element configured to generate a first signal representative of an acoustic sound, a second housing, comprising a coupling member that couples to an anchor system that is configured to be surgically implanted into the skull of a recipient, an electronics module configured to process the first signal and generate a second signal, and a transducer that vibrates in response to the second signal and wherein the second housing is separate from the first housing such that the transducer vibrations are substantially reduced in the first housing.

In another aspect of the invention, a method of implanting a bone conduction hearing device to reduce acoustic feedback is disclosed. The method comprises: positioning a first housing adjacent the skull of a recipient at a first location, the first housing including a sound input element configured to receive an acoustic signal; surgically implanting an anchor into the skull of the recipient at a second location, the second location remote from the first location; and coupling a second housing to the anchor, the second housing separate from the first housing, and including a transducer configured to receive a signal representative of the acoustic sound signal and to vibrate such that the recipient perceives the acoustic signal as sound.

In another aspect of the invention, a system for reducing the acoustic feedback in a bone anchored hearing device is provided. The system comprises: a sound input element configured to generate a first signal representative of an acoustic sound; and a transducer separate from the sound input element and coupled to an anchor system that is configured to be surgically implanted into the skull of a recipient, the transducer configured to be in communication with and remote from the sound input element and vibrate such that the recipient perceives the acoustic sound and feedback percept is reduced.

BRIEF DESCRIPTION OF THE DRAWINGS

Illustrative embodiments of the present invention are described herein with reference to the accompanying drawings, in which.

DETAILED DESCRIPTION

Embodiments of the present invention are generally directed to a bone conduction device for converting a received acoustic sound signal into a mechanical force for delivery to a recipient's skull. The bone conduction device includes a housing having a sound input component, such as microphone, to receive the acoustic sound signal, an electronics module configured to generate an electrical signal representing the acoustic sound signal, and a transducer to convert the electrical signal into a mechanical force for delivery to the recipient's skull. The transducer is configured to generate vibrations substantially along one displacement axis.

Figure 1:
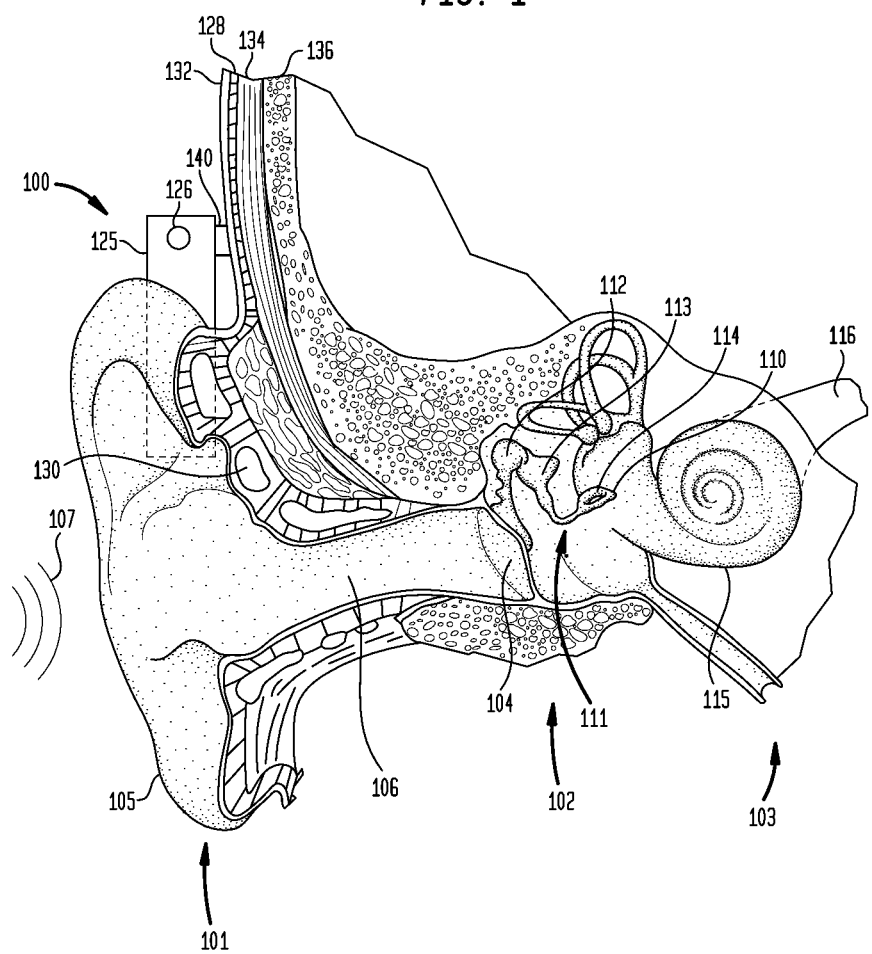
FIG. 1 is a perspective cutaway view of a human ear and a bone conduction device implanted behind the ear in which embodiments of the present invention may be advantageously implemented.

FIG. 1 is a perspective view of embodiments of a bone conduction device 100 in which embodiments of the present invention may be advantageously implemented. In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates cochlear hair cells (not shown). Cochlear hair cells come in two anatomically and functionally distinct types: the outer and inner hair cells. Activation of one or more types of these hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 may be positioned behind outer ear 101 of the recipient.

In the embodiments illustrated in FIG. 1, bone conduction device 100 comprises a housing 125 having a microphone 126 positioned therein or thereon. Housing 125 is coupled to the body of the recipient via coupling 140. As described below, bone conduction device 100 may comprise a sound processor, a transducer, transducer drive components and/or various other electronic circuits/devices.

In accordance with embodiments of the present invention, an anchor system (not shown) may be implanted in the recipient. As described below, the anchor system may be fixed to bone 136. In various embodiments, the anchor system may be implanted under skin 132 within muscle 134 and/or fat 128. In certain embodiments, a coupling 140 attaches device 100 to the anchor system.

Figure 2A:
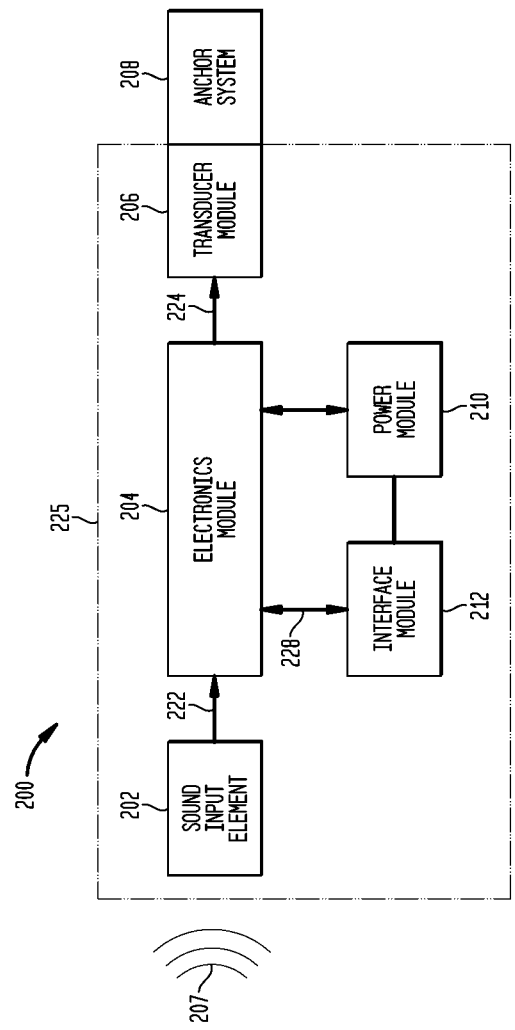
FIG. 2A is a functional block diagram of an embodiment of a bone conduction device in accordance with one embodiment of the present invention.

A functional block diagram of one embodiment of bone conduction 100, referred to as bone conduction device 200, is shown in FIG. 2A. In the illustrated embodiment, a sound 207 is received by a sound input element 202. In some embodiments, sound input element 202 is a microphone configured to receive sound 207, and to convert sound 207 into an electrical signal 222. As described below, in other embodiments sound 207 may received by sound input element 202 as an electrical signal.

As shown in FIG. 2A, electrical signal 222 is output by sound input element 202 to an electronics module 204. Electronics module 204 is configured to convert electrical signal 222 into an adjusted electrical signal 224. As described below in more detail, electronics module 204 may include a sound processor, control electronics, transducer drive components, and a variety of other elements.

As shown in FIG. 2A, a transducer 206 receives adjusted electrical signal 224 and generates a mechanical output force that is delivered to the skull of the recipient via an anchor system 208 coupled to bone conduction device 200. Delivery of this output force causes one or more of motion or vibration of the recipients skull, thereby activating the hair cells in the cochlea via cochlea fluid motion.

FIG. 2A also illustrates a power module 210. Power module 210 provides electrical power to one or more components of bone conduction device 200. For ease of illustration, power module 210 has been shown connected only to interface module 212 and electronics module 204. However, it should be appreciated that power module 210 may be used to supply power to any electrically powered circuits/components of bone conduction device 200.

Bone conduction device 200 further includes an interface module 212 that allows the recipient to interact with device 200. For example, interface module 212 may allow the recipient to adjust the volume, alter the speech processing strategies, power on/off the device, etc. Interface module 212 communicates with electronics module 204 via signal line 228.

In the embodiment illustrated in FIG. 2A, sound pickup device 202, electronics module 204, transducer 206, power module 210 and interface module 212 have all been shown as integrated in a single housing, referred to as housing 225. However, it should be appreciated that in certain embodiments of the present invention, one or more of the illustrated components may be housed in separate or different housings. Similarly, it should also be appreciated that in such embodiments, direct connections between the various modules and devices are not necessary and that the components may communicate, for example, via wireless connections.

Figure 2B:
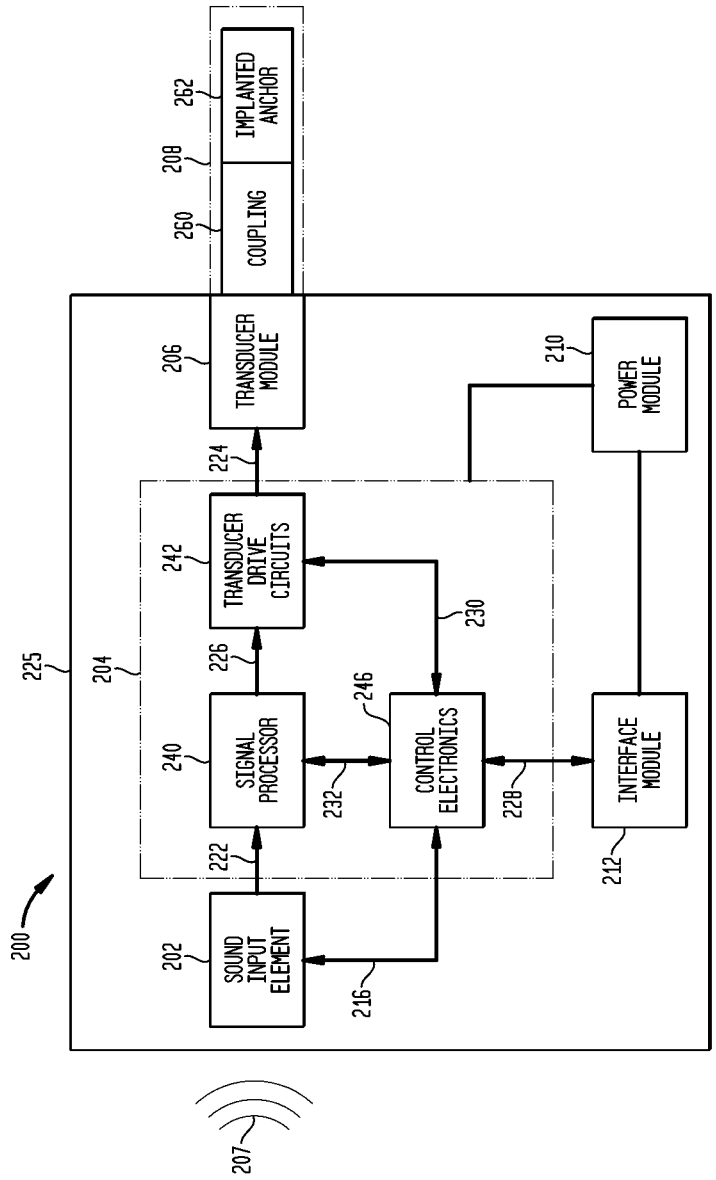
FIG. 2B is a more detailed functional block diagram of the bone conduction device of FIG. 2A in accordance with one embodiment of the present invention.

FIG. 2B provides a more detailed view of bone conduction device 200 of FIG. 2A. In the illustrated embodiment, electronics module 204 comprises a sound processor 240, transducer drive components 242 and control electronics 246. As explained above, in certain embodiments sound input element 202 comprises a microphone configured to convert a received acoustic signal into electrical signal 222. In other embodiments, as detailed below, sound input element 202 receives sound 207 as an electrical signal.

In embodiments of the present invention, electrical signal 222 is output from sound input element 202 to sound processor 240. Sound processor 240 uses one or more of a plurality of techniques to selectively process, amplify and/or filter electrical signal 222 to generate a processed signal 224A. In certain embodiments, sound processor 240 may comprise substantially the same sound processor as is used in an air conduction hearing aid. In further embodiments, sound processor 240 comprises a digital signal processor.

Processed signal 226A is provided to transducer drive components 242. Transducer drive components 242 output a drive signal 224B, to transducer 206. Based on drive signal 224B, transducer 206 provides the output force to the skull of the recipient.

For ease of description the electrical signal supplied by transducer drive components 242 to transducer 206 has been referred to as drive signal 224B. However, it should be appreciated that processed signal 224B may comprise an unmodified version of processed signal 224A.

As noted above, transducer 206 generates an output force to the skull of the recipient via anchor system 208. As shown in FIG. 2B, anchor system 208 comprises a coupling 260 and an implanted anchor 262. Coupling 260 may be attached to one or more of transducer 206 or housing 225. For example, in certain embodiments, coupling 260 is attached to transducer 206 and vibration is applied directly thereto. In other embodiments, coupling 260 is attached to housing 225 and vibration is applied from transducer 206 through housing 225.

As shown in FIG. 2B, coupling 260 is coupled to an anchor implanted in the recipient, referred to as implanted anchor 262. As explained with reference to FIG. 3, implanted anchor 262 provides an element that transfers the vibration from coupling 260 to the skull of the recipient.

As noted above, a recipient may control various functions of the device via interface module 212. Interface module 212 includes one or more components that allow the recipient to provide inputs to, or receive information from, elements of bone conduction device 200.

As shown, control electronics 246 may be connected to one or more of interface module 212, sound pickup device 202, sound processor 240 and/or transducer drive components 242. In embodiments of the present invention, based on inputs received at interface module 212, control electronics 246 may provide instructions to, or request information from, other components of bone conduction device 200. In certain embodiments, in the absence of user inputs, control electronics 246 control the operation of bone conduction device 200.

Figure 3:
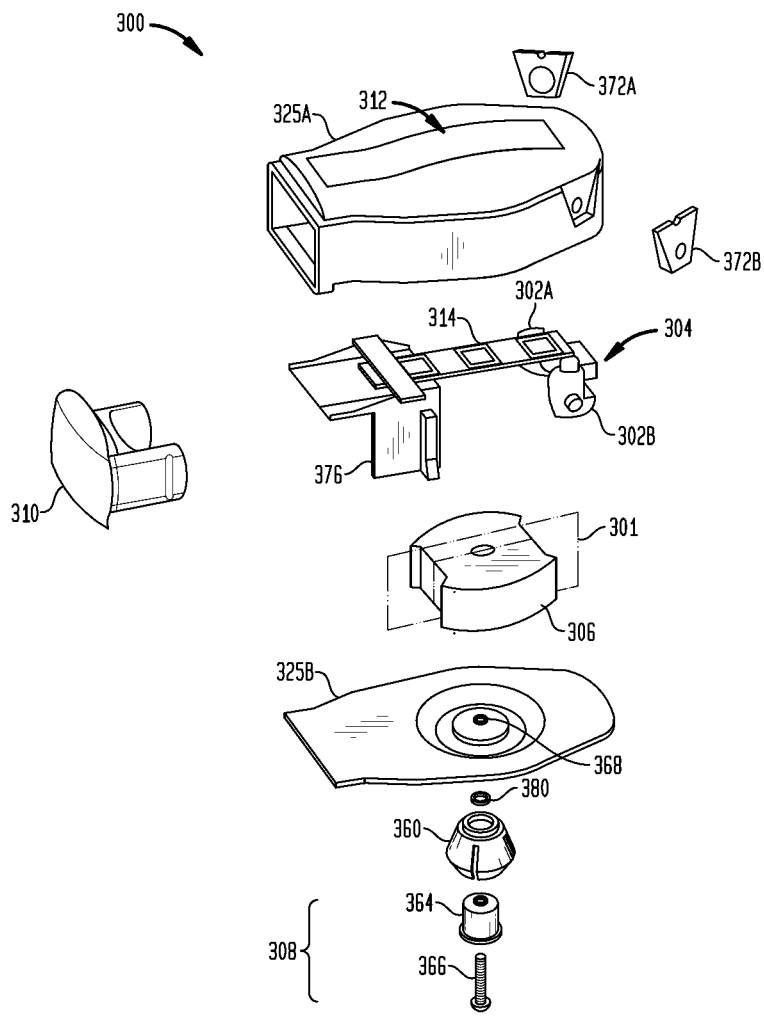
FIG. 3 is an exploded view of an embodiment of a bone conduction device in accordance with one embodiment of FIG. 2B in accordance with one embodiment of the present invention.

FIG. 3 illustrates an exploded view of one embodiment of bone conduction 200 of FIGS. 2A and 2B, referred to herein as bone conduction device 300. As shown, bone conduction device 300 comprises an embodiment of electronics module 204, referred to as electronics module 304. As explained above, included within electronics module 304 are a sound processor, transducer drive components and control electronics. For ease of illustration, these components have not been illustrated in FIG. 3.

In the illustrated embodiment, electronics module 304 includes a printed circuit board 314 (PCB) to electrically connect and mechanically support the components of electronics module 304. Attached to PCB 314 are one or more sound input elements, shown as microphones 302 to receive a sound.

In the illustrated embodiment, bone conduction device 300 further comprises battery shoe 310 for supplying power to components of device 300. Battery shoe 310 may include one or more batteries. In certain embodiments, PCB 314 is attached to a connector 376. Connector 376 is configured to mate with battery shoe 310. In certain embodiments, connector 376 and battery shoe 310 may be releasably snap-locked to one another. Furthermore, in such embodiments, one or more battery connects (not shown) are disposed in connector 376 to electrically connect battery shoe 310 with electronics module 304.

In the embodiment illustrated in FIG. 3, bone conduction device 300 further includes a two-part housing 325, comprising first housing portion 325A and second housing portion 325B. Housing portions 325 are configured to mate with one another to substantially seal bone conduction device 300.

In the embodiment of FIG. 3, first housing portion 325A has an opening therein for receiving battery shoe 310. In such embodiments, battery shoe protrudes through first housing portion 325A and may be removed or inserted by the recipient. Also in the illustrated embodiment, microphone covers 372 are releasably attached to first housing portion 325A. Microphone covers 372 provide a barrier over microphones 302 to protect microphones 302 from dust, dirt or other debris.

Bone conduction device 300 further includes an embodiment of interface module 212, referred to herein as interface module 312. Interface module 312 is configured to provide or receive user inputs from the recipient.

Also as shown in FIG. 3, bone conduction device 300 comprises an embodiment of transducer 206, referred to as transducer 306. Transducer 306 generates an output force that causes movement of the cochlea fluid so that a sound may be perceived by the recipient. The output force may result in mechanical vibration of the recipient's skull, or in physical movement of the skull about the neck of the recipient. As noted above, in certain embodiments, bone conduction device 300 delivers the output force to the skull of the recipient via an anchor system 308. Anchor system 308 comprises a coupling 360 and implanted anchor 362. In the embodiment illustrated in FIG. 3, coupling 360 is configured to be attached to second housing portion 325B. As such, in this embodiment, vibration from transducer 306 is provided to coupling 360 through housing 325B. In the embodiment shown in FIG. 3, an opening 368 is provided in second housing portion 325B. A screw (not shown) may be inserted through opening 368 to attach transducer 306 to coupling 360. In such embodiments, an O-ring 380 may be provided to seal opening 368 around the screw.

As noted above, anchor system 308 includes implanted anchor 362. Implanted anchor 362 comprises a bone screw 366 implanted in the skull of the recipient and an abutment 364. In an implanted configuration, screw 366 protrudes from the recipient's skull through the skin. Abutment 364 is attached to screw 366 above the recipient's skin. In other embodiments, abutment 364 and screw 366 may be integrated into a single implantable component. Coupling 360 is configured to be releasably attached to abutment 364 to create a vibratory pathway between transducer 306 and the skull of the recipient.

In alternative embodiments of the present invention, bone conduction device 300 may comprise one or more additional sound input element. For example, bone conduction device 300 may comprises an electrical input. In such embodiments, the electrical input is configured to connect device 300 to external equipment and receive an electrical sound signal directly therefrom. The electrical input may permit bone conduction device 300 to be connected to, for example, FM hearing systems, MP3 players, televisions, mobile phones, etc.

In still other embodiments, a further sound input element in the form of a telecoil may be integrated in, or connected to, bone conduction device 300. The telecoil permits bone conduction device 300 to receive input signals from, for example, a telephone or other similar device.

Figure 4A:
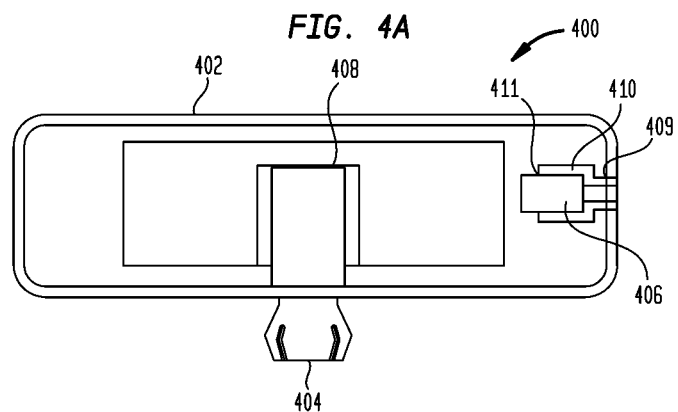
FIG. 4A is a schematic diagram of a bone conduction device with an internal sound input element suspended from the housing via a vibration dampening coupling member.

FIG. 4A illustrates one embodiment of bone conduction device 200, depicted as bone conduction device 400, which includes a housing 402 and a coupler 404 for removeably attaching the housing 402 to an anchor, such as anchor 262 (FIG. 2B). In this embodiment, the housing 402 includes, among other components, a microphone or sound input element 406 and a transducer 408. Additionally, the housing may include a sound processor, an electronics module, a power source and an interface (each of each is not shown), or any other suitable component, as described herein. The sound input element, as described above, receives sound waves, which are sent to the sound processor. Sound processor in turn may amplify or alter the signal and send this altered signal to the transducer to impart vibrations to the anchor.

In one embodiment, sound input element 406 is suspended from the housing or coupled to any other suitable portion of the bone anchored device 400 using flexible shaft or vibration dampening coupling member 410. By attaching the sound input element in this manner, the sound input element may be isolated from the mechanical vibrations generated by the transducer, thus reducing feedback through the sound input element. In other words, the recipient of the bone conduction device will have feedback percept substantially reduced or eliminated.

In one embodiment, the sound input element is mounted internally of housing 402. The coupling member may be a rubber sleeve or other configuration that is configured to allow the sound input element to frictionally fit therein. In one embodiment, coupling member may be coupled to the sound input element via opening 411 at one end thereof that allows access to an internal space therein. The sound input element may have a diameter slightly larger than opening 411, thus creating a secure, but removable fit for the sound input element. In other embodiments, the coupling is a connector formed of other suitable material, such as silicon, foam and/or any other suitable material or combination of materials. It is noted that each of these materials may have a different spring constant or ability to dampen the vibrations.

In one embodiment, coupling member 410 is coupled to housing 402 at point or location 409 and to the sound input element 406 at a point or location 413. In this embodiment, the vibrations imparted to the sound imparted to the sound input element are reduced or attenuated from point or location 409 to point or location 413. In other words, due to the spring constant and the attenuation of the coupling member 410, the vibrations imparted to the sound input element are reduced along the length of the coupling member 410.

In some embodiments, an additional vibration absorbing material may disposed between the coupling member and the sound input element to further attenuate the vibrations generated by said transducer. For example, the coupling member may be a rubber sleeve and the additional vibration material may be a layer of foam between the coupling and the sound input element.

In one embodiment, the coupling may be a spring or flexible shaft with a low spring constant; however, the spring constant may be any desired spring constant. The flexible shaft may be formed from metal or plastic or any other suitable material or combination of materials. In this embodiment, the sound input element may be detachable from the housing, such that the spring constant or stiffness of the flexible shaft may be easily changeable or selectable as the power levels of the bone conduction device increase or changes. In other words, some spring constants my produce less feedback based on the amplitude of vibration of the transducer. In this embodiment, the flexible shaft may be selected from a plurality of flexible shafts, each flexible shaft having a different spring constant or stiffness.

Figure 4B:
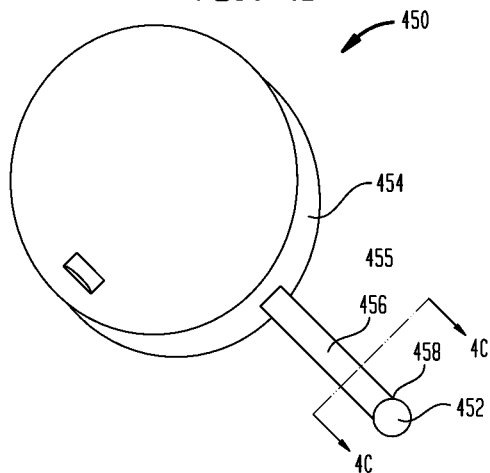
FIG. 4B is a top perspective view of a bone conduction device with a sound input element mounted externally to said housing via a vibration dampening coupling member.
Figure 4C:
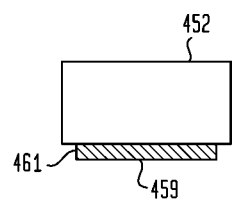
FIG. 4C is a cross sectional view of the flexible connector of FIG. 4B taken along line 4C-4C in FIG. 4B.

FIG. 4B illustrates one embodiment of bone conduction device 200, depicted as bone conduction device 450. In this embodiment, bone conduction device 450, is substantially similar to device 400; however, sound input element or microphone 452 is mounted externally of housing 454 at point or location 458. In this embodiment, vibration dampening coupling member is flexible shaft or extension 456 that extends outwardly and externally from housing 454. In some embodiments, the shaft 456 has a substantially rectangular cross section, wherein the width 459 is substantially greater than its height 461 (FIG. 4C). The sound input element is coupled to the shaft at point or location 458 along the width 459. Such a configuration will enable the shaft to attenuate the vibrations imparted to the sound input element. In this embodiment, the vibrations imparted to the sound imparted to the sound input element are reduced or attenuated from or location 455 to point or location 458. In other words, due to the spring constant and the attenuation of the shaft 456, the vibrations imparted to the sound input element are reduced along the length of the shaft 456. By mounting the sound input element externally in such a manner, feedback is isolated, while allowing for the remaining components to contribute to the mass that is vibrated.

The flexible shaft may be formed from any suitable flexible material, such as rubber, metal, plastic, silicon, and/or any other suitable material or the flexible shaft may be a spring, as described above. Disposed at the distal end 458 of the flexible shaft is sound input element 452. As with the embodiment of FIG. 4A, an additional vibration absorbing material may disposed between the coupling member and the sound input element to further attenuate the vibrations generated by said transducer.

Additionally, the sound input element and/or the flexible shaft may be detachable form the housing, such that the flexible shaft may be selected from a plurality of flexible shafts, each flexible shaft having a different spring constant or stiffness. Typically, the spring constant is be changed or selected based on the power level of the output of the transducer; however, any suitable spring constant may be selected. As with the above described embodiments, housing 454 generally includes a transducer, an electronics module, an interface and a power module (each of which is not shown), or any other suitable component, as described herein.

Figure 4D:
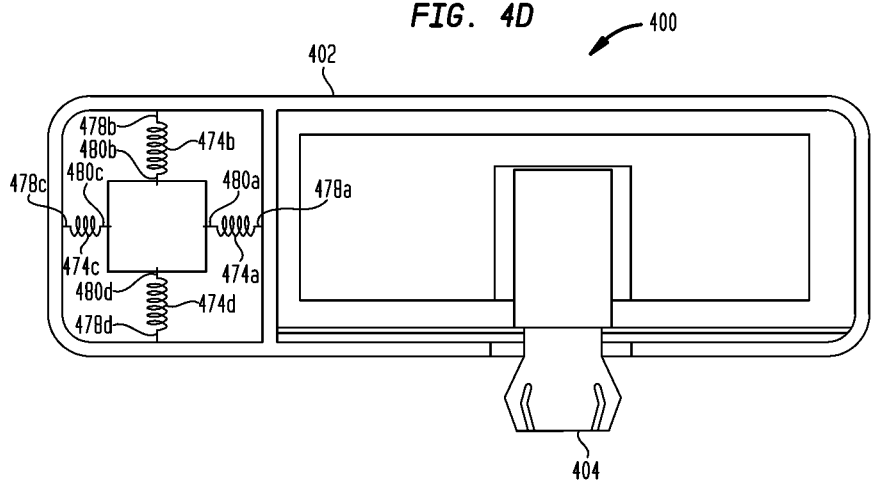
FIG. 4D is a schematic diagram of a bone conduction device with an internal sound input element suspended from the housing via a plurality of vibration dampening coupling member.

FIG. 4D illustrates another embodiment of bone conduction device 200, depicted as bone conduction device 470. In this embodiment, bone conduction device 470, is substantially similar to device 400; however, sound input element or microphone 472 is mounted using a plurality of vibration dampening coupling members 474*a-d*. In this embodiment, each of the vibration dampening coupling members 474*a-d* may a spring configured to reduce or attenuate the vibrations imparted to the sound input element 472. Each vibration dampening coupling members 474*a-d* is coupled to the housing 476 at a first or location 478*a-d*, respectively, and coupled to the sound input element 472 at a second or location 480*a-d*, respectively. As described above, the vibrations imparted to the sound input element are reduced or attenuated from points or locations 478*a-d* to points or locations 480*a-d*. In other words, due to the spring constant and the attenuation of the shaft 456, the vibrations imparted to the sound input element are reduced along the length of the vibration dampening coupling members 474*a-d*.

As with the embodiments described herein, vibration dampening coupling members 474*a-d* may be removable and replaceable by other vibration dampening coupling members having different spring constants or vibration dampening properties. Additionally, each vibration dampening coupling members 474*a-d* may have different vibration dampening properties.

Figure 5A:
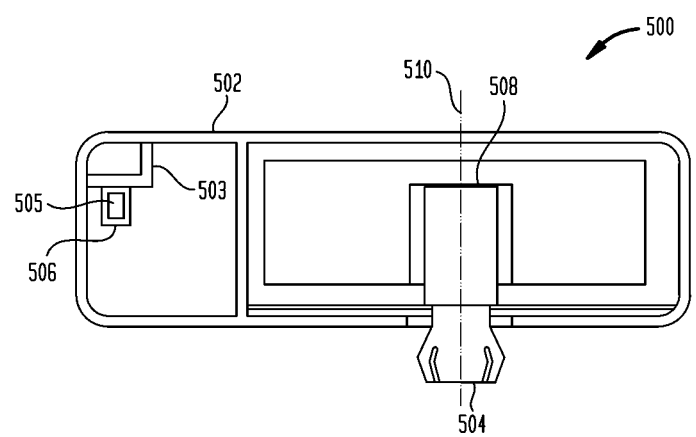
FIG. 5A is a schematic diagram of a bone conduction device with a microphone positioned such that a diaphragm of the microphone is oriented substantially parallel to the transducer vibrations in accordance with one embodiment of the present invention.

FIG. 5A illustrates one embodiment of bone conduction device 200, depicted as bone conduction device 500. As described above, conduction device 500 may include a housing 502 and a coupler 504 for removeably attaching the housing 502 to an anchor, such as anchor 262 (FIG. 2B). In this embodiment, housing 502 includes, among other components, a microphone or sound input element 506 connected to housing 502 via extension arms 503, and a transducer 508. As with the above described embodiments, housing 502 may included, an electronics module, an interface and a power module (each of which is not shown), or any other suitable component. The sound input element, as described above, receives sound waves, which are sent to the sound processor. Sound processor in turn may amplify or alter the signal and send this altered signal to the transducer to impart vibrations to the anchor, along a displacement axis 510.

In one embodiment, sound input element is positioned and arranged such that the moveable component such as a diaphragm 505 of the sound input element 506 is configured to vibrate or move due to acoustic sound is substantially parallel with displacement axis 510. As such, movable component 505 vibrates along a vibration axis that is substantially orthogonal with displacement axis 510.

Figure 5B:
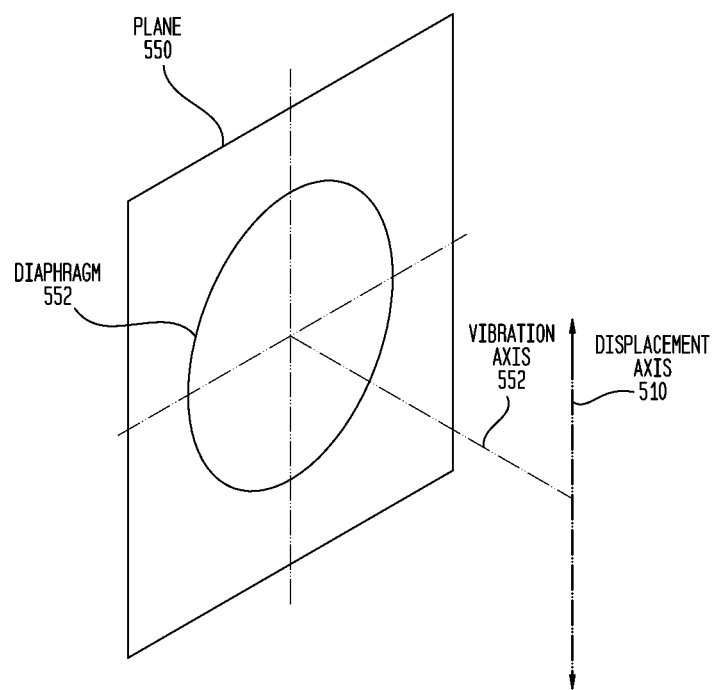
FIG. 5B is a schematic diagram showing the relative orientation of a diaphragmatic microphone and its concomitant vibration axis and the displacement axis of the transducer, in accordance with one embodiment of the present invention.

FIG. 5B is a schematic diagram of an exemplary moveable component, diaphragm 558 of a sound input element (not shown) according to one embodiment of the present invention. As illustrated, movable component 558 is mounted such that its sound impinging surface resides in a plane 550 which is substantially parallel to displacement axis 510. By configuring the moveable component to be positioned in a plane that is substantially parallel to the displacement axis, the moveable component vibrates along a vibration axis 552 that is substantially orthogonal with displacement axis 510. Thus, the feedback to the sound input element is reduced or substantially eliminated.

Figure 5C:
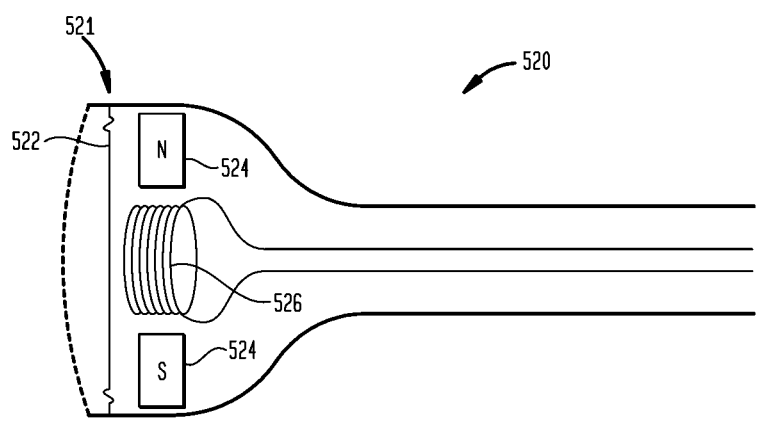
FIG. 5C is a simplified diagram of a dynamic microphone in accordance with one embodiment of the present invention.

FIG. 5C illustrates an embodiment of the sound input element for bone conduction device 500 in which the sound input element is shown as dynamic microphone 520. Microphone 520 generally includes a housing 521 which encloses a movable component or diaphragm 522, a magnet 524 and internal wiring 526 that conveys the signal to an amplifier. The microphone is configured to operate by having the diaphragm vibrate when contacted by sound. The diaphragm is attached to and thus, vibrates internal wiring 526, which is configured as a coil. The movement of the coil in the magnetic field generates small changes in electrical pressure or voltage, producing a varying current in the coil through electromagnetic induction.

Figure 5D:
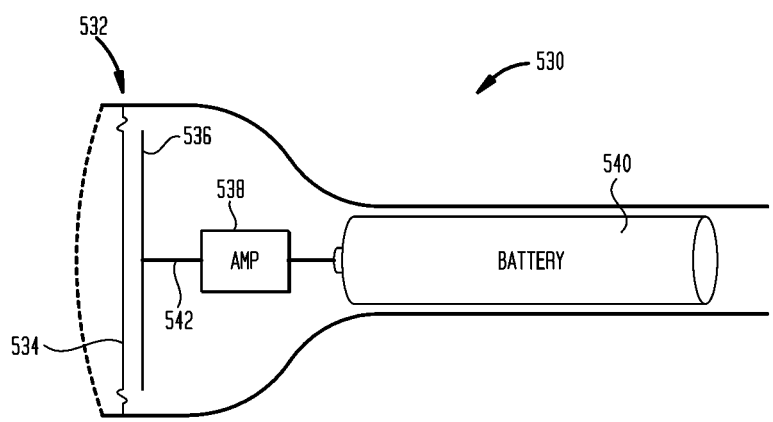
FIG. 5D is a simplified diagram of a condenser microphone in accordance with one embodiment of the present invention.

FIG. 5D illustrates an embodiment of the sound input element in which the sound input element is shown as a condenser microphone 530. Microphone 530 includes a housing 532 which encloses a movable component or diaphragm 534, a plate 536, an amp 538 and a battery 540. In this embodiment, diaphragm 534 and plate 536 are oppositely charged such that when moved closer or farther apart, a change in voltage is created. This voltage change or audio signal is then transmitted through wiring 542. Since the change in voltage is typically small (e.g., a millionth of a volt) the signal may be amplified by amp 538. The electrical charge may be a direct current voltage supplied by battery 540 and may be applied through the same wiring 542 that carries the alternating current voltage of the audio signal.

In some embodiments, the diaphragm of a microphone (e.g., diaphragm 522 or 534) may be the moveable component that resides in a plane parallel to the displacement axis 510. By configuring the diaphragm to reside or be positioned in a plane that is substantially parallel to the displacement axis, the diaphragm does not vibrate or the vibrations are reduced when the transducer vibrates. Thus, the feedback to the microphone will be reduced or substantially eliminated. It is noted that the embodiments shown in FIGS. 5C and 5D are merely exemplary and the invention is not limited to microphones or sound input devices having these types of diaphragms.

In one embodiment, transducer 508 is a piezoelectric transducer that is configured to control the amplitude of the vibrations in the direction of the displacement axis. The range of the output force of the transducer 508 may be preselected by the clinician or the recipient to accommodate certain threshold limits for the recipient's hearing. The output force for the transducer is generally a function of the mass and the velocity of the transducer 508 moving along the displacement axis 510 and the mass of the moving part of the transducer.

In one embodiment, the sound input element is mounted on a movable shaft. The movable shaft is configured to adjust the sound input element to coincide with the displacement axis. Thus, in this embodiment, a clinician or the recipient may adjust the direction of the movable shaft to improve the sound percept of the recipient.

To achieve the most desired feedback reduction, the recipient's sound percept any be determined in any suitable manner. For example, the recipient may listen to acoustic sound using the bone conduction device. The sound input element may then be adjusted on the moveable shaft to more precisely coincide with the displacement axis. This adjustment may be made manually or using any other suitable device. Once the sound input element is adjusted, the recipient's sound percept may be determined again. This procedure may be repeated until optimum feedback reduction.

Figure 6A:
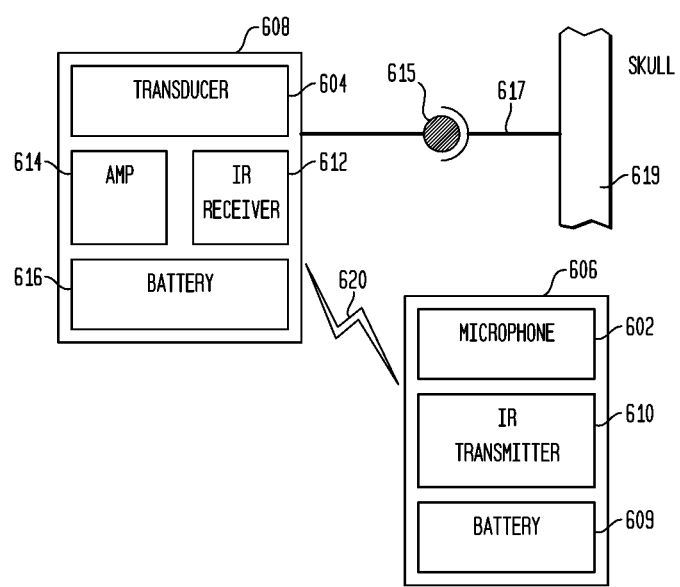
FIG. 6A is a system block diagram of a bone conduction device with a bone anchored housing and a separate microphone housing.
Figure 6B:
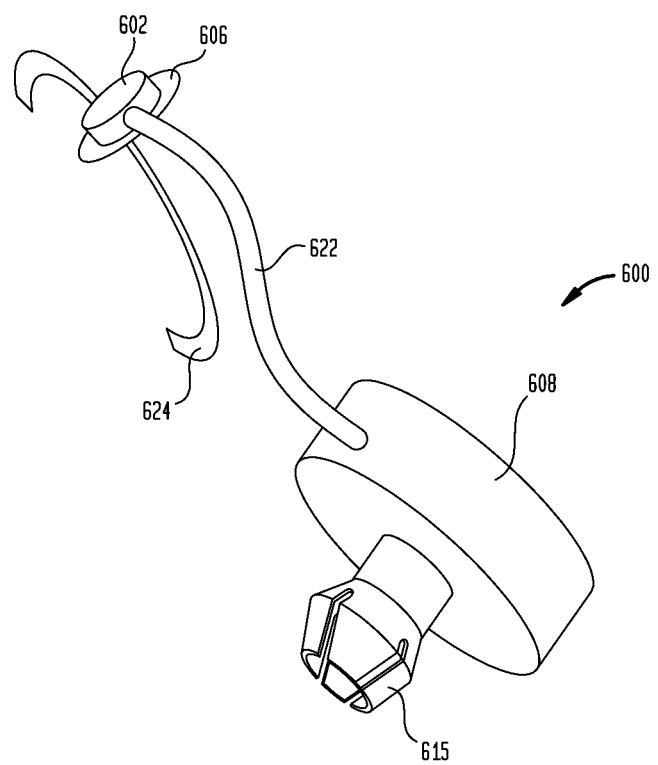
FIG. 6B is a perspective view of a bone conduction device having a microphone separated from the bone anchored housing.

FIGS. 6A and 6B illustrate embodiments of bone conduction device 200, depicted as bone conduction device, in which a sound input element or microphone 602 is located in a separate housing, remote from transducer 604, to reduce feedback percept by a recipient. By positioning the second housing remote from the first housing, transducer vibrations are substantially reduced in the sound input element.

In this embodiment, bone conduction device 600 includes a first housing 606 and a second housing 608. First housing 606 includes microphone or sound input element 602, a battery 609 and an IR transmitter 610. Second housing includes transducer 604, an IR receiver 612, an amp 614, electronics module (e.g., 204), an interface (e.g., 212) and a battery 616. It is noted that the components included in each housing are merely exemplary and each housing may include any components desired, as long as the microphone and the transducer are positioned in separate housings. The components of bone conduction device 600 operate in substantially similar manner to those described above.

In some embodiments, first housing 606 is positioned behind the ear or in the ear; however, first housing 606 may be positioned in any suitable area or place on the recipient. For example, housing 606 may be positioned in the ear, behind the ear, remotely from the ear or any other portion of the recipient's body. In another embodiment, housing 606 may be implanted or attached to skull 619. Second housing 608 may be removeably attached to the anchor 617 using a coupling member 615 in a substantially similar manner as described in the above embodiments or in any other manner described herein.

In this embodiment, bone conduction device 600 operates in a similar manner as described above; however, the signal 620 from the sound input element 602 is sent via an infrared (IR) link 618. By separating the sound input element from the transducer, the microphone is not subject to the direct vibrations within housing 608 and thus, feedback is reduced. It is noted that communication between the microphone and the transducer may be any type of wireless communication (e.g., IR, radio frequency (RF) or any other suitable communications) or the communications can be through a wired connection. In the wired connection, the device would communicate in a substantially similar to described above, except the signal from the microphone would be sent to housing 608 through an external wire, as discussed below.

It is noted that, in this embodiment, the housings 606 and 608 do not necessarily need to house the above described components and each housing may have positioned therein any of the above described or other suitable components positioned therein, as long as the sound input element and the transducer are separate. For example, in one embodiment, second housing 608 may only include transducer 604 battery, IR receiver 612 and a battery 616, while housing 606 contains the remainder of the components.

In some embodiments, as depicted in FIG. 6B, the microphone or sound input element is connected via wires 622 to housing 608. In this embodiment, housing 608 may include all the bone conduction hearing device components other than sound input element 602. As noted housing 606 may be a small platform to which sound input element is attached. In this embodiment, feedback may be isolated, while allowing for the remaining components to contribute to the mass that is vibrated.

Microphone 602 may be connected to the ear using clip 624 or in any suitable manner. For example, microphone may be positioned in or on the ear, on any portion of the recipient's head and/or body. Thus, the microphone may be concealed in a suitable area or may be attached to the body, ear or head for optimum reception.

Figure 7:
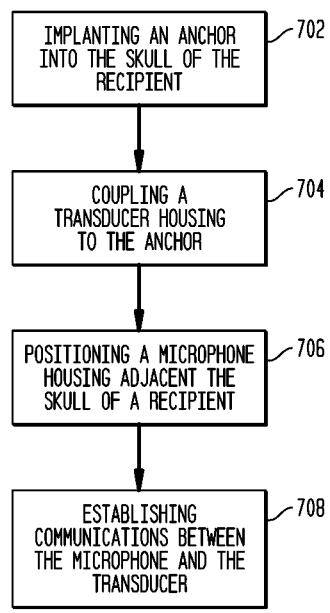
FIG. 7 is a flow chart illustrating the implantation of the bone conduction device of FIGS. 6A and 6B in accordance with one embodiment of the present invention.

FIG. 7 illustrates the general procedure for implanting the bone conduction device 600. As noted in block 702, an anchor (e.g., anchor 262) is implanted into the skull of the recipient. As discussed above, the anchor system may be fixed to bone 136. In various embodiments, the anchor system may be implanted under skin 132 within muscle 134 and/or fat 128. In block 704, a housing that includes a transducer (e.g., 608) is coupled to the anchor.

At block 706, a housing that includes a microphone is positioned adjacent the skull of the recipient (e.g., housing 606). As discussed herein, the microphone housing may be placed in the ear, behind the ear or any suitable position on the recipient. Communications between the transducer housing and the microphone housing may then be established, at block 708. such communications may be wireless or wired and may use any type of communication described herein.

Further features and advantages of the present invention are described in U.S. Provisional Application No. 61/041, 185, entitled "Bone Conduction Devices For The Rehabilitation OF Hearing Disorders," filed Mar. 31, 2008. This application is hereby incorporated by reference herein.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A bone conduction hearing device, comprising:
   a first assembly comprising a housing and a sound input element configured to generate a first signal representative of an acoustic sound; and
   a second assembly, comprising:
   a coupling member configured to couple the second assembly to an anchor site of a recipient's bone,
   an electronics module configured to process the first signal and generate a second signal, and
   a transducer that vibrates in response to the second signal, wherein the second assembly is physically separate from the first assembly such that the transducer vibrations are substantially reduced in the first assembly,
   wherein the transducer is configured to vibrate the coupling member such that the coupling member vibrates the recipient's bone at the anchor site when the coupling member is coupled to the anchor site such that the recipient perceives the acoustic sound.

2. A bone conduction hearing device, comprising:
   a first assembly comprising a housing and a sound input element configured to generate a first signal representative of an acoustic sound; and a second assembly, physically separate from the first assembly, the second assembly comprising:

an electronics module configured to process the first signal and generate a second signal, wherein the electronics module and the sound input element are communicably coupled via wireless communication, and a transducer that vibrates in response to the second signal, wherein the second assembly is configured to be coupled to an anchor system configured to anchor into a bone of the recipient so as to vibrate the bone.

3. The bone conduction device of claim 2, wherein the wireless communication occurs at a transmission frequency in the radio frequency or infrared frequency range.

4. The bone conduction device of claim 1, wherein the electronics module and the sound input element are communicably coupled via a conductor.

5. The bone conduction device of claim 1, wherein the first assembly is configured to be inserted into an ear canal of the recipient.

6. The bone conduction device of claim 1, wherein the first assembly is configured to be positioned behind an outer ear of the recipient.

7. The bone conduction device of claim 1, wherein the first assembly further comprises a power source for the sound input element.

8. The bone conduction device of claim 1, wherein the second assembly further comprises a power source for the sound input element.

9. The bone conduction device of claim 1, wherein the first assembly further comprises a power source for the transducer.

10. The bone conduction device of claim 1, wherein the second assembly further comprises a power source for the transducer.

11. The bone conduction device of claim 1, wherein the sound input element comprises a microphone.

12. The bone conduction device of claim 1, wherein the coupling member is coupled to the recipient via an anchor system that is configured to be surgically implanted into bone at the anchor site of the recipient.

13. The bone conduction hearing device of claim 1, wherein the second assembly further comprises a second assembly housing containing the electronics module and the transducer.

14. The bone conduction hearing device of claim 12, wherein the anchor system comprises a bone screw configured for implantation in a skull bone of the recipient and an abutment configured to penetrate outer skin of the recipient and be coupled to the bone screw.

15. The bone conduction hearing device of claim 2, wherein the transducer is configured to vibrate the anchor system through the outer skin so as to vibrate the skull bone.

* * * * *